United States Patent [19]

Glamkowski et al.

[11] Patent Number: 4,761,411
[45] Date of Patent: * Aug. 2, 1988

[54] DIHYDROBENZOPYRROLOBENZODIAZE-PINES USEFUL FOR TREATING PYSCHOSES

[75] Inventors: Edward J. Glamkowski, Warren; Yulin Chiang, Morristown, both of N.J.

[73] Assignee: Hoechst-Roussel Pharmaceuticals Inc., Somerville, N.J.

[*] Notice: The portion of the term of this patent subsequent to May 5, 2004 has been disclaimed.

[21] Appl. No.: 495,569

[22] Filed: May 18, 1983

[51] Int. Cl.[4] .................. A61K 31/495; C07D 403/04
[52] U.S. Cl. ..................................... 514/219; 514/220; 540/556; 540/576; 544/373; 548/469
[58] Field of Search ..................... 260/243.3; 514/219, 514/220; 540/576, 556

[56] References Cited

U.S. PATENT DOCUMENTS 4,186,199 1/1980 Glamkowski et al. ............ 260/243.3
4,192,874 3/1980 Glamkowski et al. ............ 260/243.3

OTHER PUBLICATIONS

Glamkowski, Chemical Abstract, vol. 93, p. 941, 46733q, Equivalent to U.S. Pat. No. 4,192,874.
Glamkowski, Chemical Abstract, vol. 93, p. 851, Z39373f.

Merck Index, p. 310, 2374, (9th Edition).

*Primary Examiner*—Donald G. Daus
*Assistant Examiner*—Cecilia Shen
*Attorney, Agent, or Firm*—Raymond R. Wittekind

[57] ABSTRACT

The invention relates to dihydrobenzopyrroloben-zodiazepines of the formula

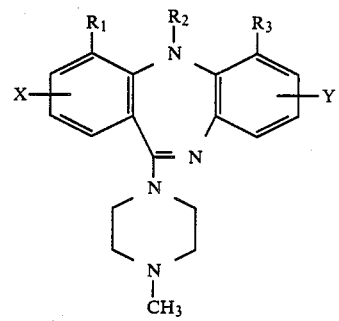

where X and Y may be the same or different and each is hydrogen, halogen, $CF_3$, lower alkyl, lower alkoxy, lower alkylthio and lower alkylsulfonyl; $R_1$ is hydrogen when $R_2$ is bonded to $R_3$ to form a $-CH_2CH_2-$ group; and $R_3$ is hydrogen when $R_1$ is bonded to $R_2$ to form a $-CH_2CH_2-$ group and the pharmaceutically acceptable acid addition salts thereof.

7 Claims, No Drawings

DIHYDROBENZOPYRROLOBENZODIAZEPINES USEFUL FOR TREATING PYSCHOSES

To the best of our knowledge the compounds of the present invention have not heretofore been described or suggested.

U.S. Pat. No. 4,186,199 discloses compounds of the formula

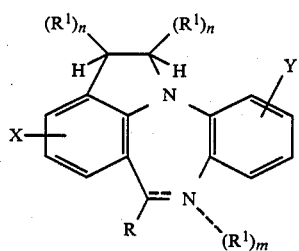

where X, Y, R and $R^1$ are various substituents and n and m are 0 or 1; which compounds have analgesic and anti-inflammatory activity. These compounds are substantially different from those of the present invention.

The compounds of the present invention have the general formula

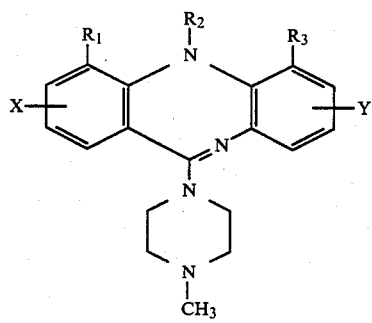

where X and Y may be the same or different and each is hydrogen, halogen, $CF_3$, lower alkyl, lower alkoxy, lower alkylthio and lower alkylsulfonyl; $R_1$ is hydrogen when $R_2$ is bonded to $R_3$ to form a $—CH_2CH_2—$ group; and $R_3$ is hydrogen when $R_2$ is bonded to $R_1$ to form a $—CH_2CH_2—$ group; and the pharmaceutically acceptable acid addition salts thereof.

Preferred embodiments of the subject invention are those where the compounds have the formula

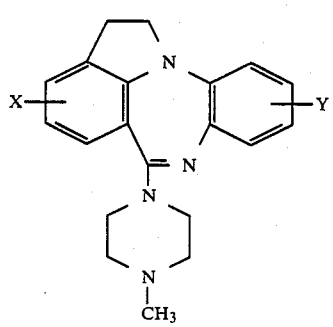

Most preferred are Compounds Ia where Y or X are independently $CH_3$ or Br.

In the above definitions the term "lower" means the group it is describing contains from 1 to 6 carbon atoms. The term "alkyl" refers to a straight or branched chain hydrocarbon containing no unsaturation, e.g. methyl, ethyl, isopropyl, 2-butyl, neopentyl, n-hexyl, etc; the term "alkoxy" refers to a monovalent substituent which consists of an alkyl group linked through an ether oxygen having its free valence bond from the ether oxygen, e.g. methoxy, ethoxy, propoxy, butoxy, pentoxy, etc.; the term "halogen" refers to a member of the family consisting of fluorine, chlorine, bromine and iodine; the term "lower alkylthio" refers to a monovalent substituent having the formula lower alkyl-S—; and the term "lower alkylsulfonyl" refers to a monovalent substituent having the formula lower alkyl-$SO_2$—. A. The compounds of the present invention are prepared in the following manner. The substituents X, Y, $R_1$, $R_2$ and $R_3$ are as defined above unless indicated otherwise. Compound I where $R_1$ is hydrogen and $R_2$ is bonded to $R_3$ to form a $—CH_2CH_2—$ group, as depicted by formula Ia

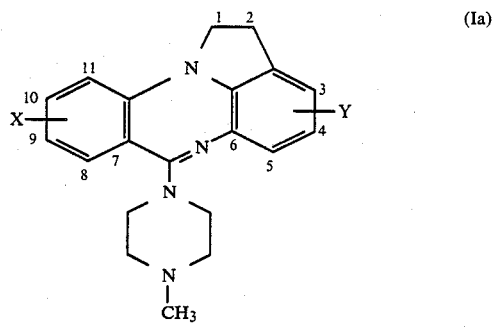

is prepared by reacting a selectes indoline of formula II,

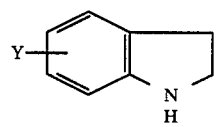

with a compound of the formula

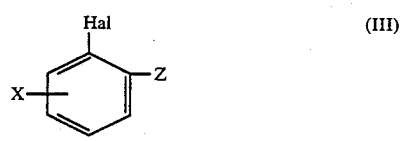

where Hal is a halogen and Z is selected from

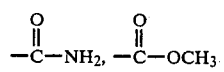

and —CN. Compound II is reacted with Compound III under conventional nucleophilic reaction conditions, typically in the presence of a base, e.g. NaH, $KOC(CH_3)_3$, $C_6H_5Li$, etc. either alone or in a solvent, e.g. dimethylsulfoxide (DMSO), dimethylformamide (DMF), etc., at a temperature of 0° C. to 100° C. for 0.5 to 24 hours, to form compound IV of the formula

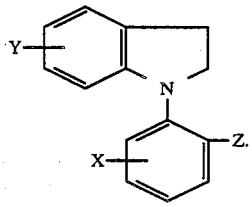
(IV)

Compound IV in turn is subjected to a conventional aromatic nitration by means of a conventional nitrating agent such as acetyl nitrate, typically by reacting Compound IV with silver nitrate and acetyl chloride in the presence of acetonitrile, to form a nitro-substituted compound of the formula

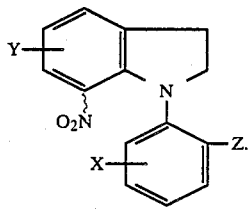
(V)

Compound V is then reduced in a conventional manner, such as catalytically e.g., with Pd in carbon catalyst, Pt on carbon, with metal salts, e.g. stannous chloride/hydrochloric acid, etc. to form a compound of the formula

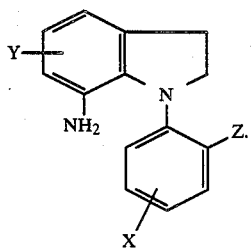
(VI)

When halogen is present at X or Y, it is preferred to use 1% Pt on carbon as the catalyst to avoid the possibility of hydrogenolysis of the nuclear halogen substituent.

Compound VI is subjected to a condensation or cyclization by reaction with a conventional agent, e.g. SiO$_2$, P$_2$O$_5$ and heating at 100° C. to 200° C. for 0.5 to 24 hours to form a benzodiazepin—one of the formula

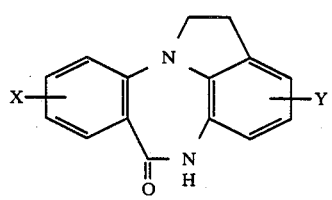
(VIIa)

when Z is

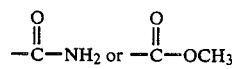

and a compound of the formula

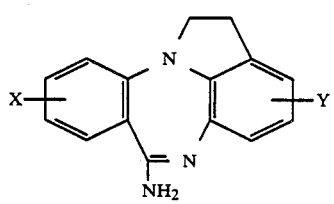
(VIIb)

when Z is —CN. Compound VII(a) or (b) in turn is reacted with N-methyl piperazine,

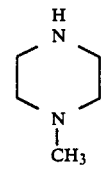

under conventional nucleophilic reaction conditions, typically in the presence of a Lewis acid, e.g. TiCl$_4$, AlCl$_3$, etc. to form Compound Ia of the invention.

Alternatively, the benzodiazepinone VIIa may be converted to Compound VIII, that is either an imino halide, as for example, an imine chloride with phosphorous oxychloride, or an iminomethylmercaptan, first by reaction with phosphorus pentasulfide in pyridine, then reaction of the resulting benzodiazepine-thione with methyl iodide.

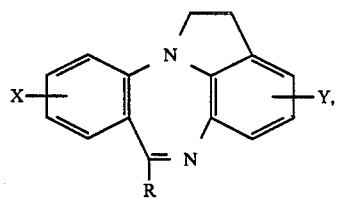
(VIII)

where R is halogen or —SCH$_3$. Compound VIII in turn is reacted with N-methyl piperazine under conventional nucleophilic conditions in an inert solvent to form compound I(a) of the invention.

Compound I where R$_1$ and R$_2$ are bonded to form a —CH$_2$CH$_2$— group, as depicted by formula Ib

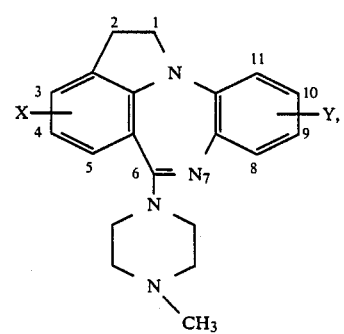
(Ib)

is prepared by reacting selected indoline II with a halo substituted nitrobenzene of the formula

where Hal is halogen. The reaction is carried out under conventional nucleophilic reaction conditions. The reaction can be carried out using an excess of the indoline to serve as a base as well as reactant. The reaction can be carried out without a solvent by heating the two reactants from 50° C. to 200° C. or in the presence of an inert solvent, e.g. benzene, toluene, xylene, dimethylformamide, etc., at a temperature of 20° C. to the boiling point of the solvent. The reaction can be carried out typically in the presence of a base, e.g. NaH, KOC(CH$_3$), n-butyllithium, etc. and an inert solvent, e.g. dimethylformamide, dimethylsulfoxide, etc., at a temperature of 0° C. to 150° C. for 0.5 to 24 hours, to form Compound X having the formula

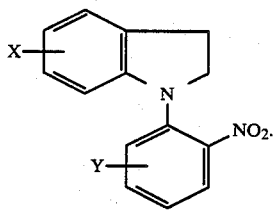

Compound X in turn is reduced, in the manner previously described, to form Compound XI

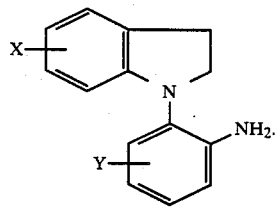

Amino-substituted Compound XI is converted to a urea XII by reaction with 4-methyl-1-piperazine carbonyl chloride,

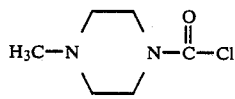

under conventional acylation conditions, typically in the presence of a base, e.g. K$_2$CO$_3$, NaHCO$_3$, collidine, etc. in an inert solvent, e.g. chloroform, dimethylformamide, toluene, etc., at a temperature of 0° C. to 100° C. for 0.5 to 48 hours to form the urea

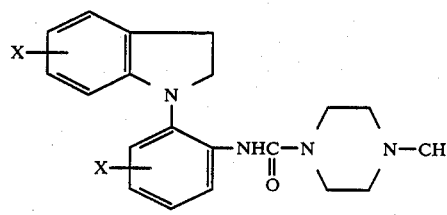

Urea XII is subjected to the cyclization reported in U.S. Pat. No. 4,186,199, which involves treating Compound XII with POCl$_3$ usually in an inert atmosphere at temperatures from 20° C. up to the reflux temperature of the reaction mixture, with or without solvent, to form Compound Ib of the invention.

The dihydrobenzopyrrolobenzodiazepines of the present invention are useful for treating psychoses by virtue of their ability to elicit an antipsychotic response in mammals.

Antipsychotic activity is determined in the climbing mice assay by a method similar to those described by P. Protais, et al., Psychopharmacol., 50, 1 (1976) and B. Costall, Eur. J. Pharmacol., 50, 39 (1978).

The subject CK-1 male mice (23-27 grams) are group-housed under standard laboratory conditions. The mice are individually placed in wire mesh stick cages (4"×4"×10") and are allowed one hour for adaption and exploration of the new environment. Then apomorphine is injected subcutaneously at 1.5 mg/kg, a dose causing climbing in all subjects for 30 minutes. Compounds to be tested for antipsychotic activity are injected intraperitoneally or given oral doses at various time intervals, e.g. 30 minutes, 60 minutes, etc. prior to the apomorphine challenge at a screening dose of 10-60 mg/kg.

For evaluation of climbing, 3 readings are taken at 10, 20 and 30 minutes after apomorphine administration according to the following scale:

| Climbing Behavior Mice with: | Score |
| --- | --- |
| 4 paws on bottom (no climbing) | 0 |
| 2 paws on the wall (rearing) | 1 |
| 4 paws on the wall (full climb) | 2 |

Mice consistently climbing before the injection of apormorphine will be discarded.

With full-developed apomorphine climbing, the animals are hanging on to the cage walls, rather motionless, over longer periods of time. By contrast, climbs due to mere motor stimulation usually only last a few seconds.

The climbing scores are individually totaled (maximal score: 6 per mouse over 3 readings) and the total score of the control group (vehicle intraperitoneally—apomorphine subcutaneously) is set to 100%. ED$_{50}$ values with 95% confidence limits, calculated by a Linear Regression Analysis, of some of the instant dihydrobenzopyrrolobenzodiazepines as well as a standard antipsychotic agent are presented in Table 1.

TABLE 1

| COMPOUND | CLIMBING MOUSE ASSAY (ED$_{50}$ mg/kg, po) |
| --- | --- |
| 9-Bromo-6-(4-methyl-1-piperazinyl)-1,2-dihydrobenzo[b]pyrrolo[3,2,1-jk] | 30.8 |

TABLE 1-continued

| COMPOUND | CLIMBING MOUSE ASSAY (ED$_{50}$ mg/kg, po) |
|---|---|
| [1,4]benzodiazepine 9-Methyl-6-(4-methyl-1-piperazinyl)-1,2-dihydrobenzo[b]pyrrolo[3,2,1-jk][1,4]benzodiazepine | 25.5 |
| clozapine | 23.2 |

Antipsychotic response is achieved when the present dihydrobenzopyrrolobenzodiazpines are administered to a subject requiring such treatment as an effective oral, parenteral or intravenous dose of from 0.01 to 50 mg/kg of body weight per day. A particularly preferred effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein ae exemplary only and they do not, to any extent, limit the scope or practice of the invention.

Some of the dihydrobenzopyrrolobenzodiazepines of the present invention are also useful as analgetics due to their ability to alleviate pain in mammals. The analgetic utility is demonstrated in the phenyl-p-quinone writhing assay in mice, a standard assay for analgesia [Proc. Soc. Exptl. Biol Med., 95 729 (1957)]. Thus, for instance, the subcutaneous dose effecting an approximately 50% inhibition of writhing (ED$_{50}$) in mice produced in this assay is as shown in Table 2.

TABLE 2

| COMPOUND | INHIBITION OF PHENYLQUINONE INDUCED WRITHING ED$_{50}$ mg/kg, sc |
|---|---|
| 9-chloro-6-(4-methyl-1-piperazinyl)-1,2-dihydrobenzo[b]pyrrolo[3,2,1-jk][1,4]benzodiazepine | 4.1 |
| 9-methyl-6-(4-methyl-1-piperazinyl)-1,2-dihydrobenzo[b]pyrrolo[3,2,1-jk][1,4]benzodiazepine | 0.34 |
| propoxyphene (standard) | 3.9 |

Analgesia production is achieved when the present dihydrobenzopyrrolobenzodiazepines are administered to a subject requiring such treatment as an effective oral, parenteral or intravenous dose of from 0.01 to 100 mg/kg of body weight per day. A particularly effective amount is about 25 mg/kg of body weight per day. It is to be understood, however, that for any particular subject, specific dosage regimens should be adjusted according to the individual need and the professional judgement of the person administering or supervising the administration of the aforesaid compound. It is to be further understood that the dosages set forth herein are exemplary only and that they do not, to any extent, limit the scope or practice of the invention.

Compounds of the invention also include:
4-chloro-6-(4-methyl-1-piperazinyl)-1,2-dihydrobenzo[b]pyrrolo[3,2,1-jk][1,4]benzodiazepine;
4-bromo-6-(4-methyl-1-piperazinyl)-1,2-dihydrobenzo[b]pyrrolo[3,2,1-jk][1,4]benzodiazepine;
4-methyl-6-(4-methyl-1-piperazinyl)-1,2-dihydrobenzo[b]pyrrolo[3,2,1-jk][1,4]benzodiazepine;
9-bromo-4-chloro-6-(4-methyl-1-piperazinyl)-1,2-dihydrobenzo[b]pyrrolo[3,2,1-jk][1,4]benzodiazepine;
4-chloro-9-methyl-6-(4-methyl-1-piperazinyl)-1,2-dihydrobenzo[b]pyrrolo[3,2,1-jk][1,4-benzodiazepine;
10-methyl-6-(4-methyl-1-piperazinyl)-1,2-dihydrobenzo[b]pyrrolo[3,2,1-jk][1,4]benzodiazepine;
9-chloro-7-(4-methyl-1-piperazinyl)-1,2-dihydrobenzo[c]pyrrolo[1,2,3-ef][1,5]benzodiazepine;
9-chloro-4-methyl-7-(4-methyl-1-piperazinyl)-1,2-dihydrobenzo[c]pyrrolo[1,2,3-ef][1,5]benzodiazepine;
4-bromo-9-chloro-7-(4-methyl-1-piperazinyl)-1,2-dihydrobenzo[c]pyrrolo[1,2,3-ef][1,5benzodiazepine.

Effective amounts of the compounds of the present invention may be administered to a subject by any one of the several methods, for example, orally as in capsules or tablets, parenterally in the form of sterile solutions or suspension, and in some cases intravenously in the form of sterile solutions. The dihydrobenzopyrrolobenzodiazepines of the present invention, while effective themselves, may be formulated and administered in the form of their pharmaceutically acceptable addition salts for purposes of stability, convenience or crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid and the like, and salts of tribasic carboxylic acids such as, for example, carboxysuccinic acid, citric acid and the like.

Effective quantities of the compounds of the invention may be administered orally, for example, with an inert diluent or with an edible carrier. They may be enclosed in gelatin capsules or compressed into tablets. For the purposes of oral therapeutic administration, the aforesaid compounds may be incorporated with an excipient and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 70% of the weight of the unit. The amount of active compound in such composition is such that a suitable dosage will be obtained. Preferred compositions and preparations according to the present invention are prepared so that an oral dosage unit form contains between 1.0–300 milligrams of the active compound.

The tablets, pills, capsules, troches and the like may also contain the following ingredients: a binder such as microcrystalline cellulose, gum tragancanth or gelatine; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 50% of the weight thereof. The amount of active compounds in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens, antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The following examples are for illustrative purposes only and are not to be construed as limiting the invention. All temperatures are given in degrees Centigrade (°C.) unless indicated otherwise.

EXAMPLE 1 a. 2-(5-Chloro-indolin-1-yl)benzamide

A slurry was prepared comprising 5-chloroindoline (15.3 gm, 0.1 mole), dimethylsulfoxide (DMSO) [50 ml] and sodium hydride (5.28 gm, 50% in oil, washed with hexane). The slurry was permitted to stir at room temperature for 1 hour. To this a solution of o-fluorobenzamide (15.2 gm, 1.1 eq.) in DMSO (20 ml) was added dropwise with the temperature between 17°–19° C. At the end of addition the reaction mixture was stirred at room temperature for 2 hours, then heated to 75°–78° C. for 16 hours. The reaction mixture was partitioned between methylene chloride (300 ml) and water (250 ml). The aqueous phase was separated and extracted twice with methylene chloride (150 ml). The combined organic solution was washed twice with water, twice with HCl (2N, 100 ml), brine (2×50 ml), dried over $Na_2SO_4$, concentrated to about 50 ml. Ether (50 ml) was added. The product was crystallized out upon standing overnight (about 16 hours). The yield was 14.2 gm (52%); m.p. 137°–138° C. Recrystallization from methylene chloride and ether yielded 2-(5-chloro-indolin-1-yl)benzamide (11.82 gm) m.p. 137°–138° C.

ANALYSIS: Calculated for $C_{15}H_{13}ClN_2O$: 66.06%C, 5.01%H, 10.29%N. Found: 65.69%C, 4.92%H, 10.18%N.

b. 2-(5-Chloro-7-nitroindolin-1-yl)benzamide

A solution of 2-(5-chloroindolin-1-yl)benzamide of Example 1a (11.9 gm), silver nitrate (8.16 gm, 1.1 equivalents), chloroform (50 ml) and acetonitrile (100 ml) was chilled at 15° C. To this a solution of acetyl chloride (3.8 gm, 1.1 equivalents) in acetonitrile (10 ml) was added dropwise in 20 minutes. The mixture was stirred at room temperature for 3 hours. The mixture was diluted with methylene chloride (250 ml) and filtered. The ppt (AgCl) was washed with a large volume of methylene chloride (1.2 l in several portions). The combined organic solution was washed twice with brine (125 ml) containing $NaHCO_3$ (2.5 gm), dried over $Na_2SO_4$, and evaporated down to a solid (14.9 gm). Recrystallization from chloroform:ether (1:1) afforded crystals of 2-(5-chloro-7-nitroindolin-1-yl)benzamide, 12.6 gm (76%), m.p. 225°–226° C.

ANALYSIS: Calculated for $C_{15}H_{12}ClN_3O_3 \cdot \frac{1}{2}CHCl_3$: 49.33%C, 3.34%H, 11.13%N. Found: 49.67%C, 3.39%H, 11.24%N.

c. 2-(5-Chloro-7-aminoindolin-1-yl)benzamide

To this solution of 2-(5-chloro-7-nitroindolin-1-yl)benzamide of Example 1b (10 gm, 26.5 mmoles) in dimethylformamide (DMF) [100 ml] and ethanol (100 ml) was added 1% Pt/carbon (2.0 gm). The mixture was shaken under hydrogen (59 psi) for 4½ hours. The mixture was then filtered under nitrogen and concentrated to remove solvent at 55° C. and high vacuum to give a solid (9.1 gm). Recrystallization from chloroform twice afforded 2-(5-chloro-7-aminoindolin-1-yl)benzamide, (4.3 gm, 47.3%), m.p. 199°–201° C. dec.

ANALYSIS: Calculated for $C_{15}H_{14}ClN_3O \cdot \frac{1}{2}H_2O$: 60.71%C, 5.06%H, 14.16%N. Found: 60.51%C, 4.68%H, 14.32%N.

d. 4-Chloro-1,2-dihydrobenzo[c]pyrrolo[1,2,3-ef][1,5]benzodiazepin-7-one 2-(5-chloro-7-aminoindolin-1-yl)benzamide of Example 1c (28.7 g, 0.10 mole) was dissolved in methanol/dichloromethane (DCM) solution (1:9 v/v) at 35° C. Silica gel (510 gm) was added to absorb the starting material, then the solvent was removed as much as possible under vacuum (50° C., 25 mmHg pressure for 1 hr.) The reaction mixture was then heated at 145°–155° C. and mechanically stirred for 1½ hours. The heating was stopped when the mixture started to turn brown. The combined material was placed onto a flash chromatography column (1 kg, silica gel 60, slurry packed with DCM), eluted with DCM (16 l) and 2% $CH_3OH$ in DCM (10 l). The fractions containing the desired product were pooled and concentrated to yield a solid, 16 gm, (59%), m.p. 252°–255° C.

ANALYSIS: Calculated for $C_{15}H_{11}ClN_2O$: 66.55%C, 4.10%H, 10.35%N. Found: 66.85%C, 4.14%H, 10.38%N.

e. 4-chloro-1,2-dihydrobenzo[c]pyrrolo[1,2,3-ef][1,5]benzodiazepin-7-one

Alternatively 4-chloro-1,2-dihydrobenzo[c]pyrrolo[1,2,3-ef][1,5]benzodiazepin-7-one can be prepared in the following manner. 2-(5-chloro-7-aminoindolin-1-yl)benzamide (2.17 gm, 7.5 mmoles) in 100 ml of hot ethanol was treated with 5 ml of ethereal-HCl solution. The red crystals formed in approximately 5 minutes. It was chilled in freezer overnight (16 hours), filtered to give 1.80 gm (89%) of pure compound with the same melting point as Example 1d.

f. 4-Chloro-7-(4-methyl-1-piperazinyl)-1,2-dihydrobenzo[c]pyrrolo[1,2,3-ef][1,5]benzodiazepine A mixture comprising toluene (250 ml), N-methylpiperazine (15 ml, 13.5 gm, 10 equivalents) and titanium tetrachloride (3 ml) was stirred for 20 minutes and then 4-chloro-1,2-dihydrobenzo[c]pyrrolo[1,2,3-ef][1,5]benzodiazepine-7-one (3.5 gm, 12.9 mmoles) was added in one portion. The resultant mixture was refluxed at 100° C. for 20 minutes, then cooled down slowly over 2 hours. The mixture was diluted with ether (500 ml) and filtered. The residue was brought into water (600 ml) and was extracted twice with ether (400 ml). The combined ether solution was washed twice with brine (150 ml) and dried over $Na_2SO_4$. Evaporation to dryness gave a solid (4.3 gm). Purification of the crude product was effected by flash chromatography over silica gel (200 gm, packed and eluted with 4% $CH_3OH$ in DCM, 1.5 l). The fractions (15 ml each) containing the pure product were pooled and concentrated to give 2.6 g (57%) of a solid. Recrystallization from ethanol yielded 2.05 gm of 4-chloro-7-(4-methyl-1-piperazinyl)-1,2-dihydrobenzo[c]pyrrolo[1,2,3-ef][1,5]benzodiazepine, m.p. 199°–200.5° C.

ANALYSIS: Calculated for $C_{20}H_{21}ClN_4$: 68.08%C, 6.00%H, 15.88%N. Found: 68.37%C, 6.08%H, 15.97%N.

EXAMPLE 2 a. 1-(4-Fluoro-2-nitrophenyl)indoline

A stirred solution of 14.9 g (0.125 mole) of indoline, 15.9 g (0.10 mole) of 2,5-difluoronitrobenzene, and 15.2 g (0.125 mole) of collidine in 100 ml of xylene was refluxed overnight (about 16 hours). After cooling to room temperature, 250 ml of dichloromethane and 250 ml of water were added with vigorous stirring. The organic phase was separated, washed twice with water, twice with 2N-HCl, once with 2N-NaOH, once more with brine, then dried and concentrated in vacuo to 19.2 g (74%) of an oil. This material was dissolved in 60 ml of iso-propyl ether from which 11.5 g (45% yield) of product crystallized. This material was recrystallized from methanol to afford 8.5 g (33% overall yield) of 1-(4-fluoro-2-nitrophenyl)indoline, m.p. 87°–89° C.

ANALYSIS: Calculated for $C_{14}H_{11}FN_2O_2$: 65.11%C, 4.29%H, 10.85%N. Found: 65.07%C, 4.41%H, 10.90%N.

b. 1-(2-Amino-4-fluorophenyl)indoline Hydrochloride

A Paar bottle, charged with 12.9 g (0.05 mole) of 1-(4-fluoro-2-nitrophenyl)indoline of Example 2a, 200 ml of absolute ethanol, 0.3 g of 5% of Pd/C, was shaken under 59 psi pressure of hydrogen until uptake ceased. The catalyst was then removed by filtration and the filtrate was concentrated to an oil weighing 11.6 g (100%). This was dissolved in 75 ml of ethanol, with heating, and then 25 ml of ether saturated with hydrogen chloride was added. An additional 400 ml of plain ether was added to maximize precipitation. The hydrochloride salt was collected, dried, and found to weigh 9.1 g (69%). Recrystallization from ethanol-ether afforded 6.8 g (52% overall yield) of 1-(2-amino-4-fluorophenyl)indoline hydrochloride, m.p. 190°–193° C.

ANALYSIS: Calculated for $C_{14}H_{13}FN_2.HCl$: 63.52%C, 5.33%N, 10.58%N. Found: 63.63%C, 5.35%H, 10.64%N.

c. N-[2-(2,3-Dihydro-1H-indol-1-yl)-5-fluorophenyl]-4-methyl-1-piperazine carboxamide Maleate To a stirred solution under nitrogen, of 50.2 g (0.22 mole) of 1-(3-amino-4-fluorophenyl)indoline of Example 2b, and 66.7 g (0.66 mole) of triethylamine in 900 ml of chloroform was added 65.7 g (0.33 mole) of 4-methyl-1-piperazine carbonyl chloride hydrochloride in portions over 5 minutes. The reaction was refluxed for 6 hours when an additional 22.2 g (0.22 mole) of triethylamine and 43.8 g (0.22 mole) of the carbonyl chloride reagent were added. After refluxing overnight (about 16 hours) the reaction was cooled, treated with 1 liter of water and stirred vigorously for 15 minutes. The layers were separated, and the organic phase was washed twice with water, dried over $Na_2SO_4$, and concentrated in vacuo to leave 50 g. This material was dissolved in 150 ml of toluene and adsorbed on a tall chromatography column containing 1.5 kg of silica gel made up in toluene. Elution first with toluene, then with increasing percentages (25% per step) of dichloromethane ($CH_2Cl_2$) in toluene, followed by 100% $CH_2Cl_2$, and finally by increasing percentages of methanol (1% per step) in $CH_2Cl_2$ brought forth 27.3 g (35% overall yield) of pure urea. 12.7 g (0.036 mole) was converted to the maleate salt in the following manner. The urea was dissolved in 30 ml of ethanol and treated with a solution of 4.64 g (0.04 ml) of maleic acid in 20 ml of warm methanol. The salt crystals were collected, and found to weigh 13.2 g (78%). Two recrystallizations from ethanol furnished N-[2-(2,3-dihydro-1H-indol-1-yl)-5-fluorophenyl]-4-methyl-1-piperazine carboxamide, maleate, m.p. 117°–120° C.

ANALYSIS: Calculated for $C_{20}H_{23}FN_4O.C_4H_4O_4$: 61.27%C, 5.78%H, 11.91%N. Found: 61.18%C, 5.94%H, 11.80%N.

d. 9-Fluoro-6-(4-methyl-1-piperazinyl)-1,2-dihydrobenzo[b]pyrrolo[3,2,1-jk][1,4]benzodiazepine A stirred mixture of 10.6 g (0.030 mole) of N-[2-(2,3-dihydro-1H-indol-1-yl)-5-fluorophenyl]-4-methyl-1-piperazine carboxamide of Example 2c in 250 ml of phosphorus oxychloride was refluxed for 6 hours under nitrogen, then cooled to room temperature. The excess phosphorus oxychloride was removed at aspirator pressure with gentle warming. The residue was chilled in an ice-bath (with exclusion of moisture) and then treated first with 250 ml of ice-cold 2N-NaOH, then with 500 ml of dichloromethane. The mixture was stirred vigorously until all the materials passed into solution. The organic phase was separated, washed thrice with water, dried over $Na_2SO_4$ and concentrated in vacuo to 9.1 g of an oil. This material was adsorbed on a tall chromatography column containing 400 g of alumina made up in $CH_2Cl_2$. Elution with $CH_2Cl_2$ brought forth fractions of pure tetracycle which were combined and concentrated to afford 3.5 g (35% overall yield) of product which crystallized. This was recrystallized from a small volume of acetone to furnish 2.1 g of 9-fluoro-6-(4-methyl-1-piperazinyl)-1,2-dihydrobenzo[b]pyrrolo[3,2,1-jk][1,4]benzodiazepine, m.p. 151°–153° C.

ANALYSIS: Calculated for $C_{20}H_{21}FN_4$: 71.41%C, 6.29%H, 16.65%N. Found: 71.07%C, 6.35%H, 16.46%N.

EXAMPLE 3 a. 1-(4-Bromo-2-nitrophenyl)indoline

A stirred solution of 29.8 g (0.25 mole) of indoline, 56.2 (0.20 mole) of 2,5-dibromonitrobenzene, and 30.3 g (0.25 mole) of collidine in 200 ml of xylene was refluxed under nitrogen overnight (about 16 hours). After cooling to room temperature, the precipitated salt was removed by filtration, and the filtrate was concentrated. The latter residue was partitioned between 300 ml of dichloromethane and 300 ml of water. The organic phase was separated, washed twice more with water, twice with dilute HCl, once with dilute NaOH, twice more with water, than dried over $Na_2SO_4$ and concentrated in vacuo leaving 55.1 g (92%). This was dissolved in 100 ml of methanol with heating from which 34.7 g (58% yield) of product crystallized. 5 g of this material was recrystallized from ethyl acetate to afford 3.5 g (70%) of 1-(4-bromo-2-nitrophenyl)indoline, m.p. 100°–102° C.

ANALYSIS: Calculated for $C_{14}H_{11}BrN_2O_2$: 52.59%C, 3.47%H, 8.78%N. Found: 52.86%C, 3.55%H, 8.81%N.

b. 1-(2-Amino-4-bromophenyl)indoline Hydrochloride

A Parr bottle, charged with 15.96 g (0.050 mole) of 1-(4-bromo-2-nitrophenyl)indoline of Example 3a, 100 ml of benzene, 100 ml of absolute ethanol, and 1.0 g of 1% Pt/carbon, was shaken under an initial 59 psi pressure of hydrogen until uptake ceased. The catalyst was then removed by filtration and the filtrate was concentrated in vacuo to an oil weighing 14.4 (100%). This was dissolved in 25 ml of ethanol, with heating, and then 25 ml of ether saturated with hydrogen chloride was added. An additional 500 ml of plain ether was added to maximize precipitation. The hydrochloride salt was collected, dried, and found to weigh 10.6 g (65%). Recrystallization twice (charcoal) from ethanol-ether afforded 4.8 g (30% overall yield) of 1-(2-amino-4-bromophenyl)indoline hydrochloride, m.p. 185°–188° C.

ANALYSIS: Calculated for $C_{14}H_{13}BrN_2 \cdot HCl$: 51.64%C, 4.33%H, 8.60%N. Found: 51.63%C, 4.42%H, 8.66%N.

c.
N-[5-Bromo-2-(2,3-dihydro-1H-indol-1-yl)phenyl]-4-methyl-1-piperazinecarboxamide Maleate To a stirred solution, under nitrogen of 43.5 g (0.15 mole) of 1-(4-bromo-2-aminophenyl)indoline of Example 3b and 82.8 g (0.60 mole) of milled potassium carbonate in 1000 ml of chloroform was added 44.7 g (0.225 mole) of 4-methyl-1-piperazinecarbonyl chloride hydrochloride in portions over 10 minutes. The reaction was refluxed for 6 hours when an additional charge of 10.4 g (0.075 mole) of potassium carbonate and 14.9 g (0.075 mole) of the carbonyl chloride reagent was added. After refluxing overnight (about 16 hours), the reaction was cooled, treated with 500 ml of water, and stirred vigorously for 15 minutes. The layers were separated and the organic phase was washed thrice with water, dried over $Na_2SO_4$, and concentrated in vacuo. The residue was dissolved in 200 ml of toluene and adsorbed on a tall chromatography column containing 1.5 kg of silica gel packed in toluene. Elution first with toluene, then with increasing percentages of dichloromethane in toluene, (25% per step), followed by dichloromethane alone, and finally with 1% methanol in dichloromethane brought forth 24 g (overall 39% yield) of fairly pure urea. This was dissolved in 100 ml of ethanol and treated with a solution of 6.96 g (0.06 mole) of maleic acid dissolved in 50 ml of ethanol. The maleate salt was collected, dried, and found to weigh 17.3 g (22% overall), m.p. 175°–177° C. dec. Recrystallization from methanol (charcoal) afforded 12.7 g (16% overall yield) of N-[5-bromo-2-(2,3-dihydro-1H-indol-1-yl)phenyl]-4-methyl-1-piperazinecarboxamide maleate, m.p. 175°–177° C. dec.

ANALYSIS: Calculated for $C_{20}H_{23}BrN_4O \cdot C_4H_4O_4$: 54.25%C, 5.12%H, 10.54%N. Found: 54.38%C, 5.04%H, 10.49%N.

d.
9-Bromo-6-(4-methyl-1-piperazinyl)-1,2-dihydrobenzo[b]pyrrolo[3,2,1-jk][1,4]benzodiazepine A stirred mixture of 9.14 g (0.022 mole) of N-[5-bromo-2-(2,3-dihydro-1H-indol-1-yl)phenyl]-4-methyl-1-piperazinecarboxamide of Example 3c in 250 ml of phosphorus oxychloride was refluxed for 7 hours under nitrogen then cooled to room temperature. The excess phosphorus oxychloride was removed at aspirator pressure with gentle warming. The residue was chilled in an ice-bath (with exclusion of moisture) and then treated first with 250 ml of ice-cold 2N-NaOH, then with 500 ml of dichloromethane. The mixture was stirred vigorously until all the material passed into solution. The organic phase was separated, washed thrice with water, dried over $Na_2SO_4$ and concentrated in vacuo to 8.5 g (98%) of an oil. This material was adsorbed on a tall chromatography column containing 350 g of alumina made up in $CH_2Cl_2$. Elution with $CH_2Cl_2$ brought forth fractions of virtually pure tetracycle which were combined and concentrated to afford 4.6 g (53% overall yield) of product as a foam. This was crystallized from a small volume of methanol to furnish 2.6 g of 9-bromo-6-(4-methyl-1-piperazinyl)-1,2-dihydrobenzo[b]pyrrolo[3,2,1-jk][1,4]benzodiazepine, m.p. 153°–155° C.

ANALYSIS: Calculated for $C_{20}H_{21}BrN_4$: 60.46%C, 5.33%H, 14.10%N. Found: 60.13%C, 5.30%H, 14.06%N.

EXAMPLE 4 a. 1-(4-Chloro-2-nitrophenyl)indoline

A stirred solution of 38.4 g (0.20 mole) of 1,4-dichloro-2-nitrobenzene and 59.6 g (0.50 mole) of indoline in 400 ml of dimethylformamide (DMF) was heated under nitrogen at 140°–145° C. alignment overnight (23 hours). The DMF solvent was then removed in vacuo and the residue was dissolved in 500 ml of dichloromethane. This solution was extracted with $H_2O$, with dilute hydrochloric acid, with brine, then dried over $Na_2SO_4$ and concentrated to an oil. This was adsorbed on a tall chromatography column containing 1.5 kg of silica gel packed in toluene. Elution with toluene brought forth 22.1 g (40% overall yield) of product, which crystallized. A small portion was recrystallized from hexane to afford 1-(4-chloro-2-nitrophenyl)indoline, m.p. 97°–99° C.

ANALYSIS: Calculated for $C_{14}H_{11}ClN_2O_2$: 61.21%C, 4.04%H, 10.20%N. Found: 60.84%C, 4.01%H, 10.22%N.

b.
N-[5-Chloro-2-(2,3-dihydro-1H-indol-1-yl)phenyl]-4-methyl-1-piperazinecarboxamide maleate To a stirred solution, under nitrogen of 24.5 g (0.10 mole) of 1-(2-amino-4-chlorophenyl)indoline (prepared from the compound of Example 4a via a method analagous to that of Example 3b) and 30.3 g (0.30 mole) of of triethylamine in 450 ml of chloroform was added 29.9 g (0.15 mole) of 4-methyl-1-piperazinecarbonyl chloride hydrochloride in portions over 5 minutes. The reaction was refluxed for 6 hours when an additional charge of 15.2 g (0.15 mole) of triethylamine and 19.9 g (0.10 mole) of the carbonyl chloride reagent was added.

After refluxing overnight (about 16 hours), the reaction was cooled, treated with 400 ml of water and stirred vigorously for 15 minutes. The layers were separated and the organic phase was washed thrice with water, dried over $Na_2SO_4$, and concentrated in vacuo. The residue was dissolved in 150 ml of toluene and adsorbed on a tall chromatography column containing 1.5 kg of silica gel packed in toluene. Elution first with toluene, then with increasing percentages of dichloromethane in toluene (25% per step), followed by dichloromethane alone, and finally increasing percentages of methanol in dichloromethane (1% per step) brought forth with 3% methanol in dichloromethane 12 g (overall 32% yield) of pure urea which crystallized. The 12 g (0.032 mole) was dissolved in 100 ml of ether, filtered, and the stirred solution was treated dropwise with a solution of 4.64 g (0.040 mole) of maleic acid in 180 ml of ether and 20 ml of ethanol. The finely divided maleate salt was collected, dried and found to weigh 10.7 g (22% overall yield). Recrystallization from 200 ml of methanol (charcoal) to which 400 ml of ether was then added afforded 7.8 g (16% overall yield) of N-[5-chloro-2-(2,3-dihydro-1H-indol-1-yl)phenyl]-4-methyl-1-piperazinecarboxamide maleate, m.p. 165°–166° C. dec.

ANALYSIS: Calculated for $C_{20}H_{23}ClN_4O \cdot C_4H_4O_4$: 59.20%C, 5.59%H, 11.51%N. Found: 59.03%C, 5.52%H, 11.14%N.

c. 9-Chloro-6-(4-methyl-1-piperazinyl)-1,2-dihydrobenzo[b]pyrrolo[3,2,1-jk][1,4]benzodiazepine A stirred solution of 6.30 g (0.017 mole) of N-[5-chloro-2-(2,3-dihydro-1H-indol-1-yl)-phenyl]-4-methyl-1-piperazinecarboxamide of Example 4b in 100 ml of phosphorus oxychloride was refluxed for 6 hours under nitrogen, then cooled to room temperature. The excess phosphorus oxychloride was removed at aspirator pressure with gentle warming. The residue was chilled in an ice-bath (with exclusion of moisture) and then treated first with 250 ml of ice-cold 2N-NaOH, then with 250 ml of dichloromethane. The mixture was stirred vigorously until all the material passed into solution. The organic phase was separated, washed four times with water, dried over $Na_2SO_4$ and concentrated in vacuo to 5.7 g (95%) of a semi-crystalline material. Recrystallization from acetone afforded 2.20 g (37% overall yield) of 9-chloro-6-(4-methyl-1-piperazinyl)-1,2-dihydrobenzo[b]pyrrolo[3,2,1-jk][1,4]benzodiazepine, m.p. 154°–156° C.

ANALYSIS:
Calculated for $C_{20}H_{21}ClN_4$: 68.08%C; 6.00%H, 15.88%N. Found: 67.85%C, 6.00%H, 15.63%N.

EXAMPLE 5 a. 1-(4-Methyl-2-nitrophenyl)indoline

A stirred mixture of 216 g (1.00 mole) of 4-bromo-3-nitrotoluene, 179 g (1.50 mole) of indoline and 182 g (1.50 mole) of collidine in 500 ml of xylene was refluxed for 3 days under nitrogen. After cooling to room temperature, the precipitated collidine hydrobromide salt was removed by filtration. The xylene filtrate was then washed with water, thrice with dilute HCl, once with dilute NaOH, again with water, then dried over $Na_2SO_4$ and concentrated to an oil. This material was dissolved in 250 ml of methanol from which 91 g (36% yield) of product crystallized having a melting point of 93°–95° C. A portion was recrystallized from methanol to afford 1-(4-methyl-2-nitrophenyl)indoline, m.p. 93°–95° C.

ANALYSIS: Calculated for $C_{15}H_{14}N_2O_2$: 70.85%C, 5.55%H, 11.02%N. Found: 70.94%C, 5.62%H, 11.08%N.

b. 1-(2-Amino-4-methylphenyl)indole Hydrochloride

A Parr bottle, charged with 15.3 g (0.060 mole) of 1-(4-methyl-2-nitrophenyl)indoline of Example 5a, 100 ml of benzene, 100 ml of absolute ethanol, and 1.00 g of 5%Pd/C catalyst, was shaken under an initial 60 psi pressure of hydrogen until uptake ceased. The catalyst was then removed by filtration and the filtrate was concentrated in vacuo to an oil weighing 13.1 g (97%). This was dissolved in 50 ml of methanol and then 50 ml of ether saturated with hydrogen chloride was added. An additional 300 ml of plain ether was added to maximize precipitation. The hydrochloride salt was collected, dried, and found to weigh 15.0 g (96%). Recrystallization twice from methanol-ether afforded 8.1 g (52% overall yield) of 1-(2-amino-4-methylphenyl)indoline hydrochloride, m.p. 203°–206° C.

ANALYSIS: Calculated for $C_{15}H_{16}N_2 \cdot HCl$: 69.09%C, 6.57%H, 10.75%N. Found: 68.97%C, 6.94%H, 10.44%N.

c. N-[5-methyl-2-(2,3-dihydro-1H-indol-1-yl)phenyl]-4-methyl-1-piperazinecarboxamide Maleate To a stirred solution, under nitrogen of 43.0 g (0.190 mole) of 1-(2-amino-4-methylphenyl)indoline of Example 5b and 105 g (0.76 mole) of milled potassium carbonate in 1000 ml of chloroform was added 56.7 (0.285 mole) of 4-methyl-1-piperazinecarbonyl chloride hydrochloride in portions over 10 minutes. The reaction was refluxed for 7 hours, when an additional charge of 13.1 g (0.095 mole) of potassium carbonate and 18.9 g (0.095 mole) of the carbonyl chloride reagent was added. After refluxing overnight (about 16 hours), the reaction was cooled, treated with 500 ml of water, and stirred vigorously for 15 minutes. The layers were separated and the organic phase was washed thrice with water, dried over $NaSO_4$, and concentrated in vacuo to a semi-solid weighing 77 g. This was dissolved in 200 ml of methanol and treated with a solution of 24.4 g of maleic acid in 100 ml of methanol. This afforded 37.7 g (43% overall yield) of crystalline maleate salt. This salt was reversed back to the free base urea, yielding 18.1 g. This material was dissolved in 50 ml of dichloromethane and absorbed on a tall chromatography column containing 300 g of silica gel packed in dichloromethane. Elution first with dichloromethane, followed by 25% methanol/75% dichloromethane brought forth 16.2 g (24% overall yield) of pure urea. This (0.046 mole) was dissolved in 50 ml of methanol and treated with a solution of 5.92 g (0.051 mole) of maleic acid dissolved in 25 ml of methanol. The resulting maleate salt was recrystallized from methanol to afford 12.6 g of N-[5-methyl-2-(2,3-dihydro-1H-indol-1-yl)-phenyl]-4-methyl-1-piperazinecarboxamide maleate, m.p. 173°–175° C. dec.

ANALYSIS: Calculated for $C_{21}H_{26}N_4O \cdot C_4H_4O_4$: 64.36%C, 6.48%H, 12.01%N. Found: 64.36%C, 6.36%H, 12.15%N.

d.
9-Methyl-6-(4-methyl-1-piperazinyl)-1,2-dihydrobenzo[b]pyrrolo[3,2,1-jk][1,4]benzodiazepine A stirred mixture of 35.1 (0.10 mole) of N-[5-methyl-2-(2,3-dihydro-1H-indol-1-yl)phenyl]-4-methyl-1-piperazinecarboxamide of Example 5c in 500 ml of phosphorus oxychloride was refluxed for 6 hours under nitrogen, then cooled to room temperature. The excess phosphorus oxychloride was removed at aspirator pressure with gentle warming. The residue was chilled in an ice-bath (with exclusion of moisture), and then treated first with 250 ml of ice-cold 2N-NaOH, then with 500 ml of chloroform. The mixture was stirred vigorously until all the material passed into solution. The organic phase was separated, washed thrice with water, and concentrated in vacuo to an oil. This was dissolved in 100 ml of boiling acetone, then allowed to crystallize at room temperature to afford 13.5 g (41% overall yield) of 9-methyl-6-(4-methyl-1-piperazinyl)-1,2-dihydrobenzo[b]pyrrolo[3,2,1-jk][1,4]-benzodiazepine, m.p. 160°-162° C.

ANALYSIS: Calculated for $C_{21}H_{24}N_4$: 75.87%C, 7.28%H, 16.85%N. Found: 75.98%C, 7.54%H, 16.48%N.

EXAMPLE 6
a.
N-[2-(2,3-Dihydro-1H-indole-1-yl)-5-($\alpha,\alpha,\alpha$-trifluoromethyl)phenyl]-4-methyl-1-piperazinecarboxamide Maleate To a stirred solution, under nitrogen of 27.8 g (0.10 mole) of 1-(2-amino-4-trifluoromethylphenyl)indoline and 30.3 g (0.30 mole) of triethylamine in 450 ml of chloroform was added 29.9 g (0.15 mole) of 4-methyl-1-piperazinecarbonyl chloride hydrochloride in portions over about 5 minutes. The reaction was refluxed for 3 hours when an additional 15.2 g (0.15 mole) of triethylamine and 15.0 g (0.075 mole) of the carbonyl chloride reagent were added. After refluxing overnight (about 16 hours), the reaction was cooled, treated with 400 ml of water and stirred vigorously for 15 minutes. The layers were separated and the organic phase was washed twice with water, dried over $Na_2SO_4$, and concentrated in vacuo to leave 41.1 g. This material was dissolved in 100 ml of 1:1 $C_6H_5CH_3:CH_2CL_2$ and absorbed on a tall chromatography column containing 1 kg of silica gel packed in toluene. Elution first with 1:1 $C_6H_5CH_3:CH_2Cl_2$, and then with 100% $CH_2Cl_2$ brought forth 20.2 g (50% overall yield) of pure urea which crystallized. 8.6 g (0.021 mole) of urea were converted to the maleate salt in the following manner. The pure urea was dissolved in 20 ml of warm ethanol and a solution of 2.67 g (0.023 mole) of maleic acid in 15 ml of ethanol was added. Then 20 ml of ether was added which caused rapid crystallization of N-[2-(2,3-dihydro-1H-indol-1-yl)-5-($\alpha,\alpha,\alpha$-trifluoromethyl)phenyl]-4-methyl-1-piperazinecarboxamide maleate. This was collected and found to weigh 8.2 g (75% yield) and had m.p. 173°-175° C. dec.

ANALYSIS: Calculated for $C_{21}H_{23}F_3N_4O.C_4H_4O_4$: 57.69%C, 5.23%H, 10.76%N. Found: 57.43%C, 5.17%H, 11.09%N.

b.
6-(4-Methyl-1-piperazinyl)-9-trifluoromethyl-1,2-dihydrobenzo[b]pyrrolo[3,2,1-jk][1,4]benzodiazepine A stirred mixture of 19.0 g (0.047 mole) of N-[2-(2,3-dihydro-1H-indol-1-yl)-5-($\alpha,\alpha,\alpha$-trifluoromethyl)phenyl]-4-methyl-1-piperazinecarboxamide of Example 6a and 190 ml of phosphorus oxychloride was heated under nitrogen to reflux. Shortly thereafter, a solution resulted and this was refluxed for 7 hours, then cooled to room temperature. The excess phosphorus oxychloride was removed at aspirator pressure with gentle warming. The residue was treated first with 400 ml of 2N sodium hydroxide solution, then with 400 ml of dichloromethane. The mixture was stirred until all the material passed into solution. The organic phase was separated, washed twice with dilute brine, dried over $Na_2SO_4$, and concentrated to 16 g (88%) of a crystalline solid. Recrystallization from acetone afforded 7.7 g (42% overall yield) of 6-(4-methyl-1-piperazinyl)-9-trifluoromethyl-1,2-dihydrobenzo[b]pyrrolo[3,2,1-jk][1,4]benzodiazepine, m.p. 177°-180° C.

ANALYSIS: Calculated for $C_{21}H_{21}F_3N_4$: 65.27%C, 5.48%H, 14.50%N. Found: 65.45%C, 5.46%H, 14.57%N.

EXAMPLE 7
a.
N-[2-(2,3-Dihydro-1H-indol-1-yl)phenyl]-4-methyl-1-piperazinecarboxamide Maleate To a stirred solution, under nitrogen, of 21.0 g (0.10 mole) of 1-(2-aminophenyl)indoline and 30.4 g (0.30 mole) of triethylamine in 400 ml of chloroform was added 29.9 g (0.15 mole) of 4-methyl-1-piperazinecarbonyl chloride hydrochloride in portions over about 5 minutes. The reaction was refluxed for 6 hours when an additional 10.1 g (0.10 mole) of triethylamine and 19.9 g (0.10 mole) of 4-methyl-1-piperazinecarbonyl chloride hydrochloride were added. After refluxing overnight (total of 25 hrs), the reaction was cooled, treated with 400 ml water, and stirred vigorously for 15 minutes. The layers were separated and the organic phase was washed twice with water, dried over $Na_2SO_4$, and concentrated in vacuo. The residue was dissolved in 100 ml of absolute ethanol and treated in one portion with a warm solution of 13.2 g (0.11 mole) of maleic acid in 50 ml of ethanol. After several hours, the crystals were collected, washed with ethanol, and dried to afford 19.2 g (43%), of product, m.p. 158° dec. An additional 4.5 g of pure salt was obtained from the mother liquor making the total amount of product 23.7 g and the yield 53%. 3.0 g of product were recrystallized from ethanol to provide 2.80 g of N-[2-(2,3-dihydro-1H-indol-1-yl)phenyl]-4-methyl-1-piperazinecarboxamide maleate.

ANALYSIS: Calculated for $C_{20}H_{24}N_4O.C_4H_4O_4$: 63.70%C, 6.24%H, 12.38%N. Found: 63.96%C, 6.25%H, 12.49%N.

b.
6-(4-Methyl-1-piperazinyl)-1,2-dihydrobenzo[b]pyrrolo[3,2,1-jk][1,4]benzodiazepine To 21.1 g (0.0627 mole) of N-[2-(2,3-dihydro-1H-indol-1-yl)phenyl]-4-methyl-1-piperazinecarboxamide of Example 7a was added 500 ml of phosphorus oxychloride and this was refluxed under nitrogen overnight. The excess $POCl_3$ was then removed at aspirator pressure with warming. The residue was boiled and triturated on the steam bath with 600 ml of absolute ethanol until solution resulted. This solution was cooled and stirred resulting in separation of a solid. This solid was collected, washed with ethanol, with ether, and finally hexane, then dried to afford 19.0 g. This was partitioned between 200 ml of chloroform and 100 ml of water, with good stirring. Addition of 2.5N-NaOH rendered the medium basic, and the product base passed into the organic phase. This was separated, washed twice with water, dried over Na$_2$SO$_4$ and concentrated to 6.5 g of an oil. This oil was boiled with 60 ml of acetone, filtered from some insolubles, and the filtrate concentrated under nitrogen to 20 ml and allowed to crystallize. This gave 2.6 g of solid, m.p. 144°–146° C. dec. This material was treated with 20 ml of 2N-HCl with stirring. The resulting solution was filtered from a small amount of insolubles, then made basic with 2.5N-NaOH and the product extracted into dichloromethane. The latter extract was washed twice with water, dried over Na$_2$SO$_4$, and concentrated to an oil which began to crystallize. This was quickly dissolved in a small volume of boiling acetone and allowed to crystallize. The crystals were collected, washed with a little acetone, and dried to afford 2.00 g (10% overall yield) of 6-(4-methyl-1-piperazinyl)-1,2-dihydrobenzo[b]pyrrolo[3,2,1-jk][1,4]benzodiazepine, m.p. 149°–151° C.

ANALYSIS: Calculated for C$_{20}$H$_{22}$N$_4$: 75.44%C, 6.96%H. Found: 75.56%C, 6.95%H.

EXAMPLE 8 a. 5-Chloro-1-(4-chloro-2-nitrophenyl)indoline

A stirred solution of 123 g (0.80 mole) of 5-chloroindoline, 134 g (0.70 mole) of 1,4-dichloronitrobenzene and 97 g (0.80 mole) of collidine in 1000 ml of dimethylformamide was heated under nitrogen at 150° C. for 48 hours. The mixture was then cooled, filtered from insolubles, and the solvent was removed in vacuo with warming. The residue was partitioned between 1000 ml of dichloromethane and 500 ml of water. The water layer was removed and the organic phase was washed twice with 2N-hydrochloric acid, once with 2N-sodium hydroxide, once more with water, dried over Na$_2$SO$_4$ and concentrated to an oil weighing 230 g. This was dissolved in 170 ml of methanol and stirred at room temperature and then at 0° C. The resultant crystals were collected, washed well with cold methanol, and dried. This afforded 86.5 g (40% yield) of product, m.p. 130°–133° C. 4 g of 5-chloro-1-(4-chloro-2-nitrophenyl)indoline were recrystallized from methanol in 85% yield (overall yield: 34%); m.p. 133°–135° C.

ANALYSIS: Calculated for C$_{14}$H$_{10}$Cl$_2$N$_2$O$_2$: 54.39%C, 3.26%H, 9.06%N. Found: 54.36%C, 3.31%H, 9.14%N.

b. 1-(2-Amino-4-chlorophenyl)-5-chloroindoline Hydrochloride Ethanolate

A Parr bottle, charged with 12.4 g (0.040 mole) of 5-chloro-1-(4-chloro-2-nitrophenyl)indoline of Example 8a, 100 ml of benzene, 100 ml of absolute ethanol and 0.5 g of 1%Pt/C was shaken under an initial hydrogen pressure of 57 psig until uptake ceased. The catalyst was then removed by filtration and the filtrate was concentrated in vacuo to an oil weighing 11.2 g (100%). This was dissolved in 30 ml of ethanol and then 30 ml of ether saturated with hydrogen chloride was added. An additional 500 ml of plain ether was added, and the mixture was stirred at 0° C., to maximize precipitation. The hydrochloride salt was collected, dried, and found to weigh 9.2 g (73%), m.p. 174°–178° C. Recrystallization from ethanol (charcoal) afforded 1-(2-amino-4-chlorophenyl)-5-chloroindoline hydrochloride ethanolate in 58% overall yield, m.p. 177°–180° C.

ANALYSIS: Calculated for C$_{14}$H$_{12}$Cl$_2$N$_2$.HCl.C$_2$H$_6$O: 53.13%C, 5.30%H, 7.75%N. Found: 53.25%C, 5.28%H, 7.78%N.

c. N-[5-Chloro-2-(5-chloroindol-2,3-dihydro-1H-1-yl)phenyl]-4-methyl-1-piperazinecarboxamide It is predicted that if the 1-(2-amino-4-chlorophenyl)-5-chloroindoline of Example 8b is employed and treated in the manner of Example 4b that N-[5-chloro-2-(5-chloroindol-2,3-dihydro-1H-1-yl)phenyl]-4-methyl-1-piperazinecarboxamide will be obtained.

d. 4,9-Dichloro-6-(4-methyl-1-piperazinyl)-1,2-dihydrobenzo[b]pyrrolo[3,2,1-jk][1,4]benzodiazepine It is predicted that if the N-[5-chloro-2-(5-chlorindol-2,3-dihydro-1H-1-yl)phenyl]-4-methyl-1-piperazinecarboxamide of Example 8c is employed and treated in the manner of Example 4c that 4,9-dichloro-6-(4-methyl-1-piperazinyl)-1,2-dihydrobenzo[b]pyrrolo[3,2,1-jk][1,4]benzodiazepine will be obtained.

EXAMPLE 9 a. 1-(4-Methoxy-2-nitrophenyl)indoline

A stirred mixture of 37.5 g (0.20 mole) of 4-chloro-3-nitroanisole, 35.8 g (0.30 mole) of indoline and 36.4 g (0.30 mole) of collidine in 100 ml of xylene was refluxed for 6 days. The mixture was then concentrated to an oil. This was partitioned between 1000 ml of dichloromethane and 500 ml of water. The organic phase was separated and extracted once more with water, then twice with dilute hydrochloric acid, once with dilute sodium hydroxide, twice more with water, then dried over sodium sulfate, and finally concentrated in vacuo, leaving an oil (38 g). This was dissolved in 150 ml of toluene and adsorbed on a tall chromatography column containing 1.5 kg of silica gel packed in toluene. Elution with toluene brought forth fractions containing 11.8 g (22% overall yield) of product which crystallized. This was recrystallized from isopropyl ether to afford 1-(4-methoxy-2-nitrophenyl)indoline, m.p. 88°–90° C.

ANALYSIS: Calculated for C$_{15}$H$_{14}$N$_2$O$_3$: 66.65%C, 5.22%H, 10.37%N. Found: 66.85%C, 5.12%H, 10.52%N.

b. 1-(2-Amino-4-methoxyphenyl)indoline

It is predicted that if 1-(4-methoxy-2-nitrophenyl)indoline of Example 9a is employed and treated in the manner of Example 5b that 1-(2-amino-4-methoxyphenyl)indoline hydrochloride will be obtained.

c. N-[2-(2,3-dihydro-1H-indol-1-yl)-5-methoxyphenyl]-4-methyl-1-piperazinecarboxamide It is predicted that if the 1-(2-amino-4-methoxyphenyl)indoline of Example 9B is employed and treated in the manner of Example 4b that N-[2-(2,3-dihydro-1H-indol-1-yl)-5-methoxyphenyl]-4-methyl-1-piperazinecarboxamide will be obtained.

d. 9-Methoxy-6-(4-methyl-1-piperazinyl)-1,2-dihydrobenzo[b]pyrrolo[3,2,1-jk][1,4]benzodiazepine It is predicted that if the N-[2-(2,3-dihydro-1H-indol-1-yl)-5-methoxyphenyl]-4-methyl-1-piperazinecarboxamide of Example 9c is employed and treated in the manner of Example 4c that 9-methoxy-6-(4-methyl-1-piperazinyl)-1,2-dihydrobenzo[b]pyrrolo[3,2,1-jk][1,4]benzodiazepine will be obtained.

EXAMPLE 10 a. 1-(4-Methylthio-2-nitrophenyl)indoline

To a stirred solution, under nitrogen, of 10.3 g (0.04 mole) of 1-(4-fluoro-2-nitrophenyl)indoline of Example 2a in 100 ml of hexamethylphosphoramide (HMPA) was added in portions 8.64 g (0.16 mole) of lithium methyl mercaptide. This resulted in a rapid exotherm from 18° to 40° C. The mixture was heated at 90° C. for 3 hours when an additional 4.32 g (0.08 mole) of lithium methyl mercaptide was added. After two more hours at 90° C., the mixture was cooled and quenched into 1 liter of ice/water, with good stirring. The product was extracted into 300 ml of ether, and the aqueous extracted twice more with ether. The combined ether phases were washed four times with water, dried over $Na_2SO_4$, and concentrated to a oil weighing 11.9 g. This was dissolved in 50 ml of toluene and adsorbed on a tall chromatography column containing 1200 g of silica gel, packed in toluene. Elution with toluene brought forth fractions containing 6.0 g (53% overall yield) of product. This was recrystallized from toluene-hexane to afford 1-(4-methylthio-2-nitrophenyl)indoline, m.p. 67°–69° C.

ANALYSIS: Calculated for $C_{15}H_{14}N_2O_2S$: 62.91%C, 4.93%H, 9.79%N. Found: 63.02%C, 5.01%H, 9.80%N.

b. 1-(2-Amino-4-methylthiophenyl)indoline

It is predicted that if the 1-(4-methylthio-2-nitrophenyl)indoline of Example 10a is treated in the manner of Example 5b that 1-(2-amino-4-methylthiophenyl)indoline will be obtained.

c. N-[5-methylthio-2-(2,3-dihydro-1H-indol-1-yl)phenyl]-4-methyl-1-piperazinecarboxamide It is predicted that if the 1-(2-amino-4-methylthiophenyl)indoline of Example 10b is treated in the manner of Example 4b that N-[5-methylthio-2-(2,3-dihydro-1H-indol-1-yl)phenyl]-4-methyl-1-piperazinecarboxamide will be obtained.

d. 9-Methylthio-6-(4-methyl-1-piperazinyl)-1,2-dihydrobenzo[b]pyrrolo[3,2,1-jk][1,4]benzodiazepine It is predicted that if the N-[5-methylthio-2-(2,3-dihydro-1H-dinol-1-yl)phenyl]-4-methyl-1-piperazinecarboxamide of Example 10c is treated in the manner of Example 4c that 9-methylthio-6-(4-methyl-1-piperazinyl)-1,2-dihydrobenzo[b]pyrrolo[3,2,1-jk][1,4]benzodiazepine will be obtained.

EXAMPLE 11 a. 1-(4-Methylsulfonyl-2-nitrophenyl)indoline

A stirred mixture of 47.7 g (0.40 mole) of indoline, 47.1 g (0.20 mole) of 4-chloro-3-nitrophenyl methyl sulfone, 36.4 g (0.30 mole) of collidine in 500 ml of xylene was refluxed under nitrogen for 2 days. The liquid was then decanted while hot from the crust of salt and concentrated. The residue was partitioned between dichloromethane and water. The organic phase was separated, washed once with water, twice with dilute HCl, once with dilute NaOH, twice more with water, then dried over $Na_2SO_4$, and concentrated. The residue was dissolved in 200 ml of hot acetone and allowed to crystallize on cooling. This afforded 40.8 g (64% yield) of product. This was recrystallized from acetone to yield 1-(4-methylsulfonyl-2-nitrophenyl)indoline, m.p. 151.5°–154°.

ANALYSIS: Calculated for $C_{15}H_{14}N_2O_4S$: 56.60%C, 4.43%H, 8.80%N. Found: 56.70%C, 4.66%H, 8.85%N.

b. 1-(2-Amino-4-methylsulfonylphenyl)indoline

It is predicted that if the 1-(4-methylsulfonyl-2-nitrophenyl)indoline of Example 11a is treated in the manner of Example 5b that 1-(2-amino-4-methylsulfonylphenyl)indoline will be obtained.

c. N-[5-Methylsulfonyl-2-(2,3-dihydro-1H-indol-1-yl)phenyl]-4-methyl-1-piperazinecarboxamide It is predicted that if the 1-(2-amino-4-methylsulfonylphenyl)indoline of Example 11b is treated in the manner of Example 4b that N-[5-methylsulfonyl-2-(2,3-dihydro-1H-indol-1-yl)phenyl]-4-methyl-1-piperazinecarboxamide will be obtained.

d. 9-Methylsulfonyl-6-(4-methyl-1-piperazinyl)-1,2-dihydrobenzo[b]pyrrolo[3,2,1-jk][1,4]benzodiazepine It is predicted that if the N-[5-methylsulfonyl-2-(2,3-dihydro-1H-indol-1-yl)phenyl]-4-methyl-1-piperazinecarboxamide of Example 11c is treated in the manner of Example 4C that 9-methylsulfonyl-6-(4-methyl-1-piperazinyl)-1,2-dihydrobenzo[b]pyrrolo[3,2,1-jk][1,4]benzodiazepine will be obtained.

EXAMPLE 12 a. N-[2-(5-Chloro-2,3-dihydro-1H-indol-1-yl)phenyl]-4-methyl-1-piperazinecarboxamide maleate To a stirred solution, under nitrogen, of 24.5 g (0.10 mole) of 1-(2-aminophenyl)-5-chloroindoline and 30.4 g (0.30 mole) of triethylamine in 400 ml of chloroform was added 29.9 g (0.15 mole) of 4-methyl-1-piperazinecarbonyl chloride hydrochloride in portions over 5 minutes. The reaction was refluxed for 6 hours when an additional 15.2 g (0.15 mole) of triethylamine and 15.0 g (0.075 mole) of the piperazinecarbonyl chloride.HCl were added. After refluxing overnight (about 16 hours), the reaction was cooled, treated with 400 ml of water, and stirred vigorously for 15 minutes. The layers were separated and the organic phase was washed twice with water, dried over $Na_2SO_4$, and concentrated. The residue was dissolved in toluene and adsorbed on a tall chromatography column containing 1.5 kg. of silica gel packed with toluene. Elution first with toluene, then with increasing percentages of dichloromethane in toluene (25% per step), followed by increasing percentages of methanol in dichloromethane (1% per step) brought forth 9.8 g of urea (26% yield), using 4% methanol in dichloromethane. A solution of 7.42 g (0.020 mole) of the urea in 50 ml of ether was treated dropwise with a solution of 2.32 g (0.020 mole) of maleic acid in 150 ml of ether. The crystals so formed weighed 6.9 g (18% overall yield), m.p. 147°–149° C. dec. This was dissolved in ethanol, boiled with charcoal, filtered and treated with ether to form 4.2 g of N-[2-(5-chloro-2,3-dihydro-1H-indol-1-yl)phenyl]-4-methyl-1-piperazinecarboxamide maleate, m.p. 150°–152° C.

ANALYSIS: Calculated for $C_{20}H_{23}ClN_4O \cdot C_4H_4O_4$: 59.20%C, 5.59%H, 11.51%N. Found: 59.06%C, 5.70%H, 11.32%N.

b.
6-(4-Methyl-1-piperazinyl)-4-chloro-1,2-dihydrobenzo[b]pyrrolo[3,2,1-jk][1,4]benzodiazepine It is predicted that if the N-[2-(5-chloro-2,3-dihydro-1H-indol-1-yl)phenyl]-4-methyl-1-piperazinecarboxamide of Example 12a is treated in the manner of Example 4c that 6-(4-methyl-1-piperazinyl)-4-chloro-1,2-dihydrobenzo[b]pyrrolo[3,2,1-jk][1,4]benzodiazepine will be obtained.

EXAMPLE 13

2-(5-Bromo-indolin-1-yl)benzamide

A slurry was prepared from 5-bromoindoline (9.85 g, 50 mmoles) dimethylsulfoxide (DMSO) (35 ml), sodium hydride (2.6 g, 50% in oil, washed with hexane, 1.1 eq). The slurry was stirred for 30 minutes. To this a solution of o-fluorobenzamide (7.9 g, 1.1 eq) in DMSO (15 ml) was added dropwise with temperature between 12°–13° C. At the end of addition the reaction mixture was stirred at ambient temperature for 4 hours, then heated up to 55° C. for 24 hours. The reaction mixture was partitioned between dichloromethane (300 ml) and water (250 ml). The aqueous phase was separated and extracted twice with dichloromethane (DCM) (150 ml). The combined DCM solution was washed twice with water (100 ml), twice with 2N HCl (100 ml), twice with brine (50 ml), dried over $Na_2SO_4$ and concentrated to a solid. Purification was on a flash chromatographic column (150 gm of silica gel) eluted with dichloromethane (DCM) (3 l). This gave 6.4 g of product (40%). Recrystallization from a small amount of ether yielded the 2-(5-bromo-indolin-1-yl)benzamide, m.p. 120°–122° C.

ANALYSIS: Calculated for $C_{15}H_{13}BrN_2O$: 56.80%C, 4.13%H, 8.83%N. Found: 57.09%C, 4.25%H, 8.90%N.

b. 2-(5-Bromo-7-nitro-1-indolinyl)benzamide

It is predicted that if the 2-(5-bromo-indolin-1-yl)benzamide of Example 13a is treated in the manner of Example 1b that 1-(5-bromo-7-nitro-1-indolinyl)benzamide will be obtained.

c. 2-(5-Bromo-7-aminoindolin-1-yl)benzamide

It is predicted that if the 2-(5-bromo-7-nitro-1-indolinyl)benzamide of Example 13b is treated in the manner of Example 1c that 2-(5-bromo-7-aminoindolin-1-yl)benzamide will be obtained.

d.
4-Bromo-1,2-dihydrobenzo[c]pyrrolo[1,2,3-ef][1,5]benzodiazepin-7-one

It is predicted that if the 2-(5-bromo-7-aminoindolin-1-yl)benzamide of Example 13c is treated in the manner of Example 1d that 4-bromo-1,2-dihydrobenzo[c]pyrrolo[1,2,3-ef][1,5]benzodiazepin-7-one will be obtained.

e.
4-Bromo-7-(4-methyl-1-piperazinyl)-1,2-dihydrobenzo[c]pyrrolo[1,2,3-ef][1,5]benzodiazepine It is predicted that if the 4-bromo-1,2-dihydrobenzo[c]pyrrolo[1,2,3-ef][1,5]benzodiazepin-7-one of Example 13d is treated in the manner of Example 1e that 4-bromo-7-(4-methyl-1-piperazinyl)-1,2-dihydrobenzo[c]pyrrolo[1,2,3-ef][1,5]benzodiazepine will be obtained.

We claim:

1. A compound of the formula

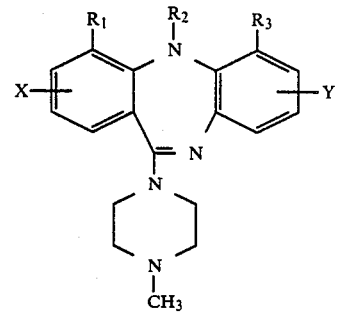

where X and Y may be the same or different and each is hydrogen, halogen, $CF_3$, lower alkyl, lower alkoxy, lower alkylthio and lower alkylsulfonyl; $R_1$ is hydrogen, when $R_2$ is bonded to $R_3$ to form a $-CH_2-CH_2-$ group and $R_3$ is hydrogen, when $R_1$ is bonded to $R_2$ to form $-CH_2-CH_2-$ group; and the pharmaceutically acceptable acid addition salts thereof.

2. The compound as defined in claim 1 which has the formula

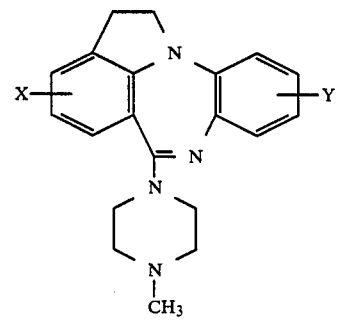

where X and Y are as previously defined or a pharmaceutically acceptable acid addition salt thereof.

3. The compound as defined in claim 1 which has the formula

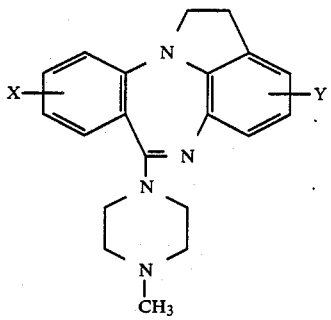

where X and Y are so previously defined or a pharmaceutically acceptable acid addition salt thereof.

4. A psychoses treating composition which comprises an amount effective in treating psychoses of a compound of the formula

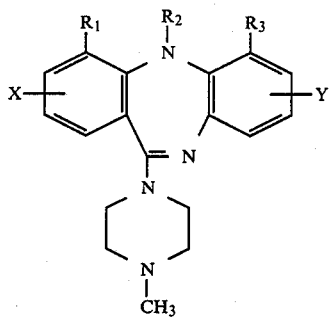

where X and Y may be the same or different and each is hydrogen, halogen, $CF_3$, lower alkyl, lower alkoxy, lower alkylthio and lower alkylsulfonyl; $R_1$ is hydrogen, when $R_2$ is bonded to $R_3$ to form a —$CH_2$—$CH_2$— and $R_3$ is hydrogen, when $R_1$ is bonded to $R_2$ to form a —$CH_2$—$CH_2$— group; and the pharmaceutically acceptable addition salts thereof.

5. The composition as defined in claim 4 wherein the compound has the formula

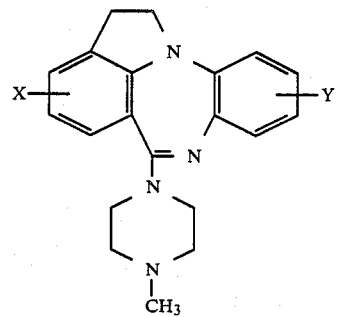

where X and Y are as previously defined or a pharmaceutically acceptable acid addition salt thereof.

6. The composition as defined in claim 4 wherein the compound has the formula

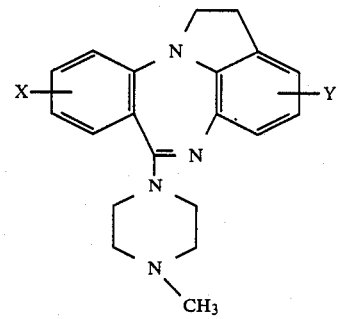

where X and Y are as previously defined or a pharmaceutically acceptable acid addition salt thereof.

7. A method of treating psychoses which comprises administering to a mammal in need of psychoses treatment a psychoses-treating effective amount of a compound as defined in claim 1.

* * * * *